(12) United States Patent
Koh (10) Patent No.: US 7,704,211 B1
(45) Date of Patent: Apr. 27, 2010

(54) METHOD AND APPARATUS FOR ASSESSING FLUID LEVEL IN LUNGS

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 1167 days.

(21) Appl. No.: 11/086,612

(22) Filed: Mar. 21, 2005

(51) Int. Cl.
*A61B 5/02* (2006.01)
*A61B 5/08* (2006.01)
*A61B 5/00* (2006.01)

(52) U.S. Cl. ................. 600/486; 600/532; 600/300

(58) Field of Classification Search ............ 128/200.24, 128/204.18, 204.21, 204.23; 600/547, 529, 600/518, 534, 527, 484, 509; 607/9, 17–20, 607/32, 59, 60, 62, 4–6
See application file for complete search history.

(56) References Cited

U.S. PATENT DOCUMENTS

| | | | | |
|---|---|---|---|---|
| 4,648,407 A | * | 3/1987 | Sackner | 600/534 |
| 5,876,353 A | * | 3/1999 | Riff | 600/547 |
| 5,911,218 A | * | 6/1999 | DiMarco | 128/200.24 |
| 6,015,388 A | * | 1/2000 | Sackner et al. | 600/529 |
| 6,473,640 B1 | | 10/2002 | Erlebacher | 600/547 |
| 6,512,949 B1 | | 1/2003 | Combs et al. | 600/547 |
| 6,595,927 B2 | | 7/2003 | Pitts-Crick et al. | 600/529 |
| 6,600,949 B1 | * | 7/2003 | Turcott | 600/518 |
| 6,641,542 B2 | * | 11/2003 | Cho et al. | 600/529 |
| 7,396,333 B2 | * | 7/2008 | Stahmann et al. | 600/529 |
| 2003/0023184 A1 | | 1/2003 | Pitts-Crick et al. | 600/547 |
| 2005/0085734 A1 | * | 4/2005 | Tehrani | 600/484 |
| 2005/0085866 A1 | * | 4/2005 | Tehrani | 607/42 |
| 2006/0247546 A1 | * | 11/2006 | Imose | 600/513 |

FOREIGN PATENT DOCUMENTS

| | | |
|---|---|---|
| EP | 1 238 630 A2 | 9/2002 |
| EP | 1 238 630 A3 | 9/2002 |
| WO | WO 98/33553 | 8/1998 |
| WO | WO 98/33554 | 8/1998 |

OTHER PUBLICATIONS

Khoo, M.C.K., "Understanding the Dynamics of State-Respiratory Interaction During Sleep," Bioengineering Approaches to Pulmonary Physiology and Medicine, Plenum Press, New York (1996); p. 7.

* cited by examiner

*Primary Examiner*—Steven O Douglas
*Assistant Examiner*—Annette F Dixon (57) ABSTRACT

The invention relates to an apparatus and method to assess the fluid level in lungs. An implantable medical device or external monitor is used to sense or monitor the patient's respiratory patterns to identify the presence of periodic breathing or Cheyne-Stokes Respiration (CSR) which is common in patients with congestive heart failure. A fluid index is used to assess the severity of congestive heart failure in a patient. A ratio of $\Delta$ blood gas/$\Sigma$total lung volume can be used to determine the lung fluid index.

15 Claims, 8 Drawing Sheets

METHOD AND APPARATUS FOR ASSESSING FLUID LEVEL IN LUNGS

FIELD OF THE INVENTION

The invention relates to patient monitoring, and more particularly, to assessing the severity of the fluid level in the lungs.

BACKGROUND

One common form of central sleep apnea, commonly known as Cheyne-Stokes respiration (CSR), is generally a breathing pattern that is first shallow and infrequent and then gradually increases to become abnormally deep and rapid, before fading away completely for a brief period. Breathing may be stopped for an extended period before the next cycle of shallow breathing begins. CSR is common in patients with congestive heart failure. Common symptoms of congestive heart failure (CHF) are shortness of breath and chest pain. These symptoms occur as a result of decreased cardiac output as well as a decreased gas exchange area due to fluid in the lungs.

Heart failure is a disease of the cardiac mechanical system: it is primarily a failure of the myocardium to meet the mechanical pumping demands required of it. In monitoring the status of a heart failure patient, measuring the mechanical hemodynamic variables is clearly desirable. However, because of the complex feedback network that monitors and controls cardiac performance, measuring variables that do not directly reflect the mechanical performance of the heart is also useful. Recognition of Cheyne-Stokes respiration via respiratory pattern analysis, hemoglobin saturation analysis, and blood gas analysis allows one to detect the presence of pulmonary edema, and thereby detect an acute heart failure exacerbation.

Many chronic diseases, such as diabetes and heart failure, require close medical management to reduce morbidity and mortality. Because the disease status evolves with time, frequent physician follow-up examinations are often necessary. At follow-up, the physician may make adjustments to the drug regimen in order to optimize therapy. This conventional approach of periodic follow-up is unsatisfactory for some diseases, such as heart failure, in which acute, life-threatening exacerbations can develop between physician follow-up examinations. It is well known among clinicians that if a developing exacerbation is recognized early, it can be easily and inexpensively terminated, typically with a modest increase in oral diuretic. However, if it develops beyond the initial phase, an acute heart failure exacerbation becomes difficult to control and terminate. Hospitalization in an intensive care unit is often required. It is during an acute exacerbation of heart failure that many patients succumb to the disease. It is often difficult for patients to subjectively recognize a developing exacerbation, despite the presence of numerous physical signs that would allow a physician to readily detect it. Furthermore, since exacerbations typically develop over hours to days, even frequently scheduled routine follow-up with a physician cannot effectively detect most developing exacerbations.

It is therefore desirable to have a method that allows the routine, frequent monitoring of patients so that an exacerbation can be recognized early in its course. With the patient and/or physician thus alerted of the need for medical intervention, a developing exacerbation can more easily and inexpensively be terminated early in its course.

SUMMARY

In one embodiment, a method is disclosed for assessing the fluid level in a patient's lungs. A first transition value is obtained for a respiration-dependent blood parameter from a first Cheyne-Stokes respiration cycle. A first tidal volume of the lungs value is obtained during the first respiration cycle. A first fluid index is calculated as a function of the first transition value and the first tidal volume of the lungs value.

In another embodiment, a method is disclosed for assessing fluid level in a patient's lungs. Measurements of transitions are accumulated in a respiration-dependent blood parameter during a first period of Cheyne-Stokes respiration. Measurements are accumulated of tidal volume of the lungs during the first period. A first fluid index is calculated as a function of the accumulated measurements of transitions and from the accumulated measurements of tidal volume during the first period. Measurements of transitions are accumulated in a respiration-dependent blood parameter during a second period of Cheyne-Stokes respiration. Measurements of tidal volume of the lungs are accumulated during the second period. A second fluid index is calculated as a function of the accumulated measurements of transitions and from the accumulated measurements of tidal volume during the second period. The first fluid index and the second fluid index are compared to obtain an indication of the fluid level in the patient's lungs.

An apparatus for assessing severity of lung fluid in a congestive heart failure patient is also described. The apparatus comprises a first sensor having an output related to blood gas levels in a patient. In addition, the apparatus comprises a second sensor having an output related to lung tidal volumes. The apparatus also comprises circuitry to determine a lung fluid index based on the blood gas levels and lung tidal volume.

Yet another embodiment is directed to a method of determining a fluid level in the lungs of a patient. The method comprises determining a blood gas level in the patient during a CSR cycle. In addition, the total tidal volume of the lungs of a patient during a CSR cycle is determined. The fluid level in the lungs based on the blood gas level and the lung tidal volume is assessed.

DETAILED DESCRIPTION

The invention relates to an apparatus and method to assess the fluid level in lungs. An implantable medical device or an external monitor is used to sense or monitor the patient's respiratory patterns to identify the presence of periodic breathing or Cheyne-Stokes Respiration (CSR). CSR is common in patients with congestive heart failure (CHF). This characteristic respiratory pattern is associated with lung-to-brain circulatory delay caused by the declining hemodynamic status of an acute heart failure exacerbation, and is thought to be an indirect result of developing pulmonary edema.

The role of gas exchange in the lungs is to remove carbon dioxide ($CO_2$) from blood and place oxygen ($O_2$) into the blood. The total removal rate of $CO_2$ or the total absorption rate of $O_2$ is dependent on the total functional alveolrae exposed to the air. The removal rate or absorption rate can be used as a heart failure surrogate trend to assess the degree of severity of congestive heart failure based on lung fluid retention.

A fluid index can be used to assess the severity of congestive heart failure in a patient. During a respiration event, such as a CSR cycle 100 (a cluster of breaths from the onset of breathing to the end of apnea) in FIG. 2B, a value for a transition in a respiration-dependent blood parameter is obtained. During the respiration event, a value for the tidal volume of the lungs is also obtained. The fluid index preferably is calculated from the ratio of these two values. A ratio of $\Delta$blood gas/$\Sigma$total tidal volume can be used to determine the lung fluid index. In this aspect, the value for the transition in a respiration-dependent blood parameter may be the difference or change in blood gas ($\Delta$ blood gas) determined from the difference between the maximum and minimum readings of the blood gas from a blood gas sensor surrogate, such as pH or saturated $O_2$. The lung tidal volume may be measured or estimated using, for instance, intrathoracic impedance, phrenic nerve activity or other techniques, such as a pneumotachometer or thermistor cannula positioned in the nose. The fluid index is preferably calculated for each respiration event, but may be calculated over many respiration events. CHF may be evaluated from the value of the lung fluid index or from changes in the lung fluid index over time.

Figure 1A:
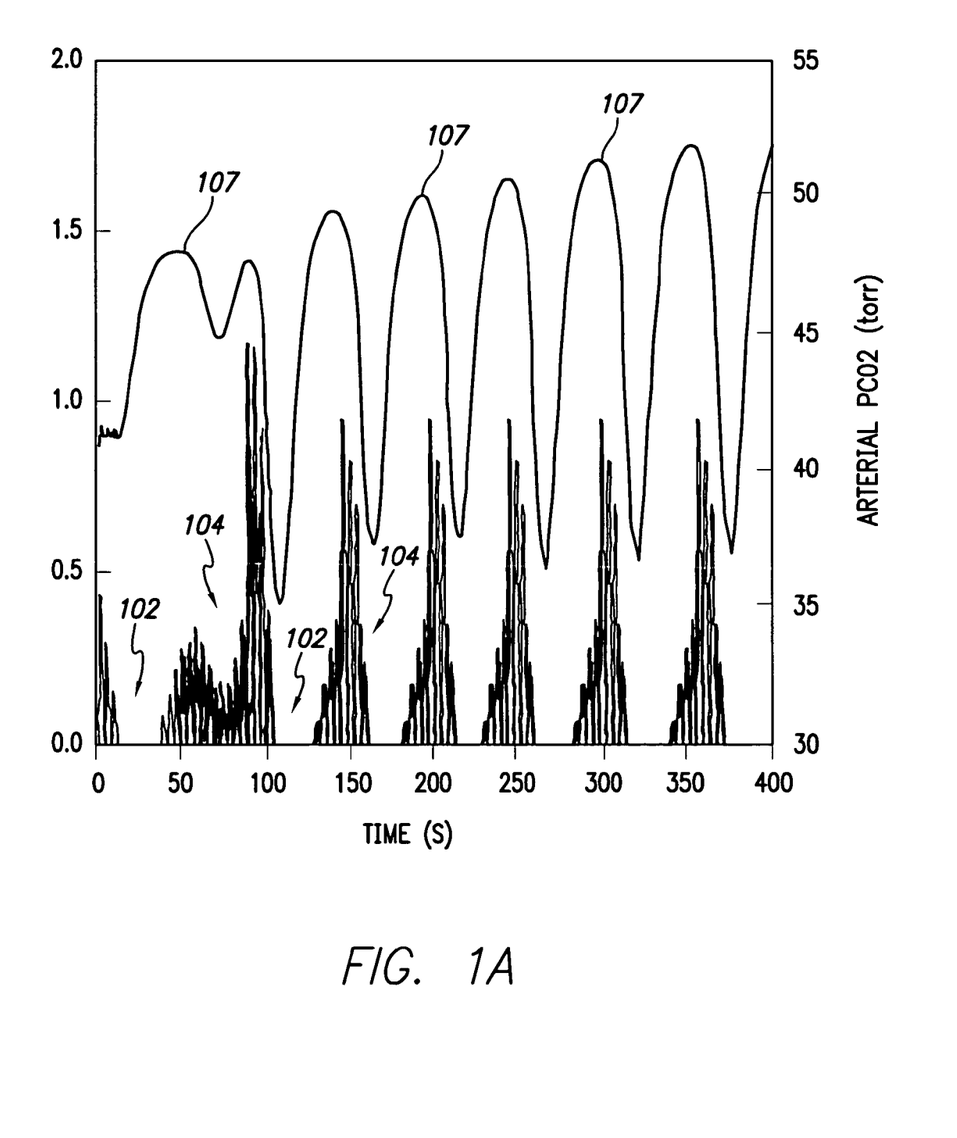
FIG. 1A is a graph that models simulation of periodic breathing during Cheyne-Stokes respiration (CSR) showing a causal relationship between carbon dioxide and the respiratory pattern.
Figure 1B:
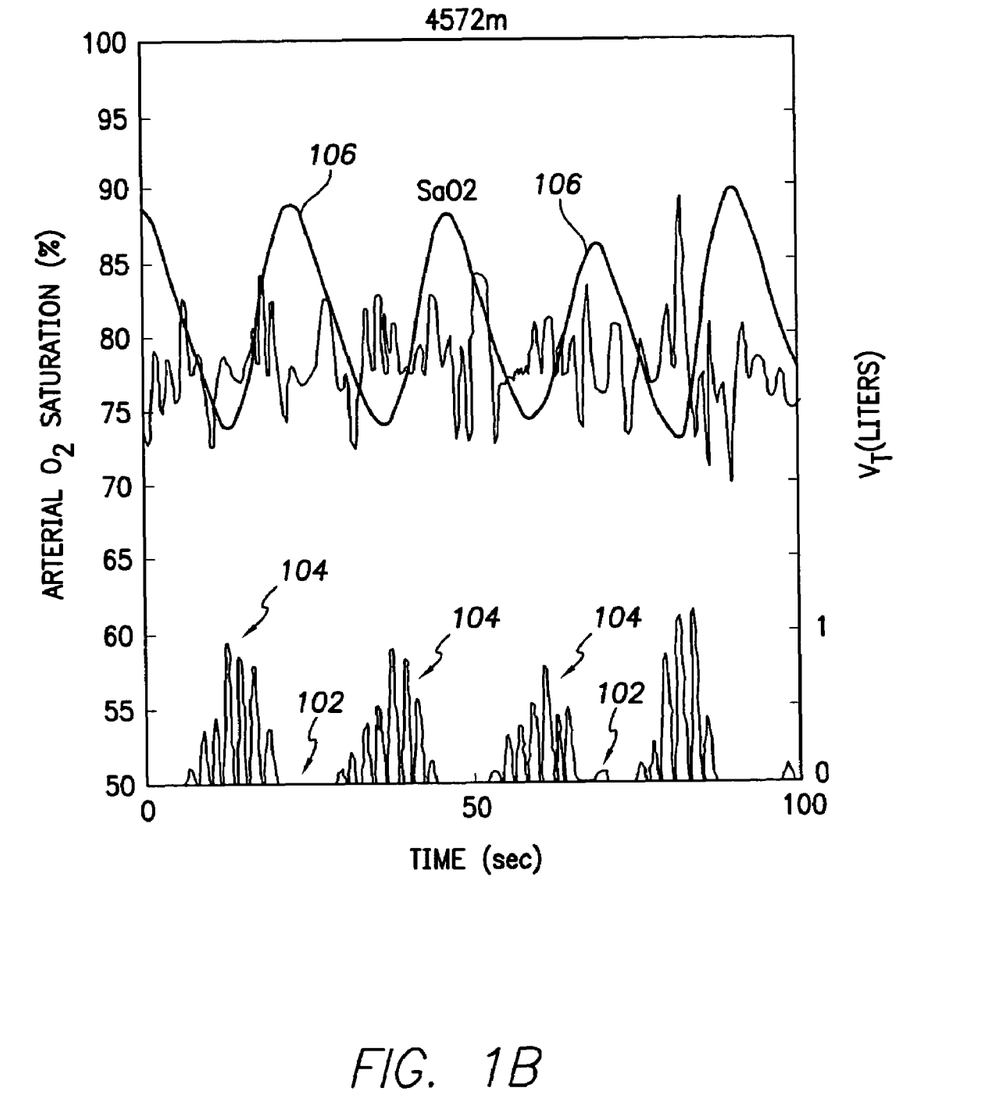
FIG. 1B is a graph that models simulation of periodic breathing during Cheyne-Stokes respiration (CSR) showing a causal relationship between oxygen saturation and the respiratory pattern.

FIG. 1A and FIG. 1B illustrate graph simulations of periodic breathing during Cheyne-Stokes respiration. FIG. 1A (Khoo, M. C. K, Understanding the Dynamics of State-Respiratory Interaction during Sleep, Bioengineering Approaches to Physiology and Medicine, Plenum Press, New York 1996) illustrates the causal relationship between arterial $CO_2$ concentration 107 and the respiratory patterns as a function of time during CSR. Periods of apnea 102 (absence of breathing) alternate with periods of hyperventilation 104. During the apneic period 102, blood $O_2$ saturation levels 106 fall (FIG. 1B) and blood $CO_2$ levels 107 increase (FIG. 1A). The increasing $CO_2$ levels result in a falling blood pH. During the periods of hyperventilation 104, when the patient is rapidly breathing, the $CO_2$ level 107 decreases as blood oxygen saturation 106 increases. FIG. 1B (Khoo, M. C. K, Understanding the Dynamics of State-Respiratory Interaction during Sleep, Bioengineering Approaches to Physiology and Medicine, Plenum Press, New York 1996) illustrates the causal relationship between saturated $O_2$ concentration 106 and respiratory patterns as a function of time, during Cheyne-Stokes respiration. Periods of apnea 102 alternate with periods of hyperventilation 104. During the apneic period 102, blood $O_2$ saturation 106 falls and blood $CO_2$ content 107 increases. During the periods of hyperventilation 104, when the patient is rapidly breathing, the $CO_2$ content 107 decreases as blood oxygen saturation 106 increases. Thus, there is a wide swing of $O_2$, $CO_2$, saturated $O_2$, and pH levels during CSR. As can be seen from FIGS. 1A and 1B, when the $CO_2$ level is high, the saturated $O_2$ level is low, with a phase shift of about 90 degrees. Since saturated $O_2$ has the same swing as $CO_2$ during apnea (taking into account the phase shift), it is possible to correlate the breathing pattern to the $CO_2$ pattern or saturated $O_2$ pattern. If a $CO_2$ waveform is not available, such as in FIG. 1A, a saturated $O_2$ waveform, such as in FIG. 1B, can be used.

Figure 2A:
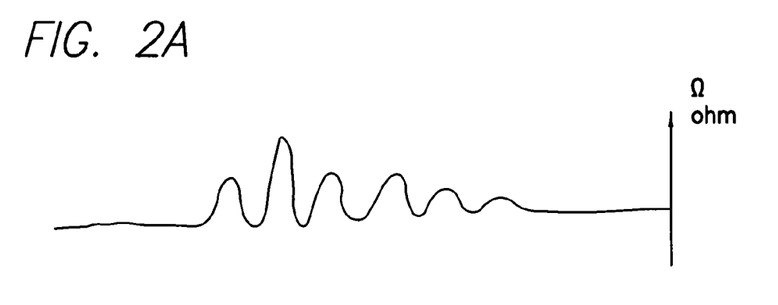
FIG. 2A is a graph that illustrates the concentration change of carbon dioxide in the blood during clusters of breathing in Cheyne-Stokes respiration.
Figure 2B:
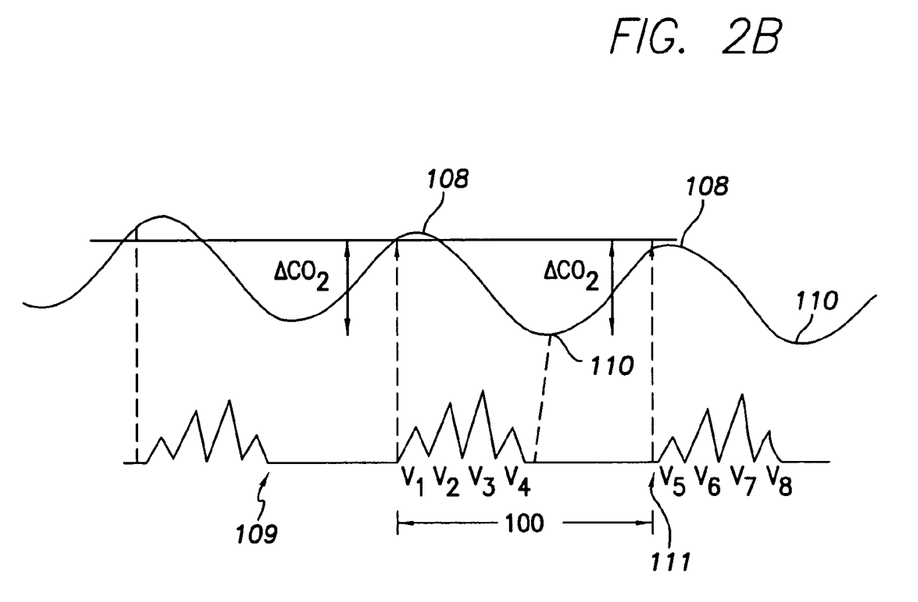
FIG. 2B is a graph showing respiratory tidal volumes representing Cheyne-Stokes respiration.
Figure 3:
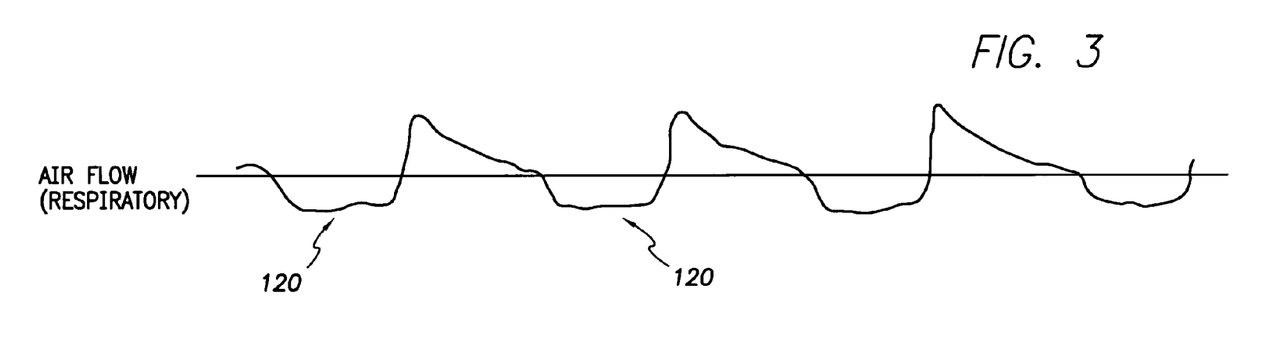
FIG. 3 is a graph that illustrates intrathoracic impedance during Cheyne-Stokes respiration.

Referring to FIGS. 2A and 2B, during monitoring for CSR, such as daily monitoring, the implantable medical device, or other monitor, acquires maximum 108 and minimum 110 readings of a blood gas, such as carbon dioxide ($CO_2$) or oxygen ($O_2$), from a blood gas surrogate such as a pH sensor or a saturated $O_2$ sensor, over a selected period of time. FIG. 2A illustrates monitoring of $CO_2$ levels over three CSR cycles. During this selected period of time, sampling times of the blood gas are adjusted automatically by monitoring the respiration pattern, such as the onset of apnea 109 to the end 111 of the next onset of apnea. From the maximum 108 and minimum 110 readings, the difference ($\Delta$ blood gas) can be calculated. The sampling frequency can vary, such as four (4) samples per second. This data acquisition sampling may occur approximately every five (5) minutes for a 30 to 40 minute time period, usually once daily. Alternatively, a given number of respiration events (CSR cycles) may be sampled. The readings may be taken more or less frequently, as determined by the health care professional. Preferably, the maximum 108 and minimum 110 values may be separately accumulated or determined from each CSR cycle and each separate difference between the maximum and minimum values is used as $\Delta CO_2$ when calculating the fluid index after each respiration event/CSR cycle. The plurality of fluid indices is then averaged.

Blood gas sampling may be used for $CO_2$ sensing. A blood gas surrogate for $CO_2$ is pH. The acidity of the blood stream can be interpolated to the $CO_2$ level by one skilled in the art since the pH level is generally the inverse of $CO_2$. The pH sensor can be positioned, for example, on a lead connected to the implantable medical device. Since the tissue is in equilibrium with the blood, the changes in chemical concentrations and pH that occur in the blood stream will be detected at the interface between the monitor housing and the tissue.

The sensor may also be an oxygen sensor which measures the oxygen saturation level in blood and subcutaneous tissue as well as the carbon dioxide level of the blood and tissue. The oxygen sensor may be positioned, for instance, on a lead that is electrically coupled to an implantable medical device, may be external, measuring the gas concentration upon exhalation, or may be percutaneous, for instance, within an abdominal patch. The leads may be implanted with the distal end situated in either the right atrium or right ventricle of the heart. In some embodiments, the oxygen sensor may be a combined $O_2$ saturation and vascular plethysmography sensor, in which the light source, preferably parallel and oppositely oriented red and infrared LEDs, are positioned such that light is directed into overlying tissue, and the light detector, preferably a photodiode, is positioned such that it collects light reflected by the overlying tissue, as discussed in U.S. Pat. No. 6,600,949, issued to Turcott, incorporated herein in its entirety.

Corresponding intrathoracic impedance or phrenic nerve activity sensing is used to estimate or measure the respiratory or lung tidal volume. In other alternative aspects, respiration is sensed using a pressure transducer placed within the pleural cavity and connected to the implantable hemodynamic monitor. Such a transducer can be placed extravascularly within the thoracic cavity, intravascularly within the venous system, or in an intracardiac position. In the latter embodiment, changes in intrathoracic pressure associated with respiration are readily detected, particularly during diastole.

Volume or pressure variations within the right ventricle or right atrium attributable to respiratory activities are sensed through intrathoracic impedance. In general, impedance mainly measures the air in the lungs. The more air present in the lungs, the higher the impedance. An intrathoracic impedance measurement is preferably obtained between an electrode (for example, a stimulation electrode, if the implanted device is a pacemaker) and the case of the implantable medical device, or alternatively, between two electrodes laid out in a rib cage. The impedance is measured by injection of a constant current of a few hundred milliamperes, at a frequency of a few Hertz, typically less than 60 Hertz.

As shown in FIG. 2B, the tidal volume of a cluster of breaths $V_1$, $V_2$, $V_3$, $V_4$ during a selected breathing period of one CSR cycle 100 is estimated or measured using intrathoracic impedance. Corresponding intrathoracic impedance peak-to-peak is used as the peak value for each breath to estimate the respiratory or lung tidal volume, as shown in the graph in FIG. 3. The selected breathing period during which the tidal volumes are measured may be for about one minute approximately every five (5) minutes for a 30 to 40 minute period, usually once daily. However, the values may be taken more or less frequently, as determined by the health care professional. The selected breathing period generally corresponds to the time period during which the maximum and minimum values for the blood gas are obtained for one CSR cycle. In FIG. 2B, each peak $V_1$, $V_2$, $V_3$, $V_4$, $V_5$, $V_6$, $V_7$, $V_8$ corresponds to a breath taken after a long apneic period, which causes a slow fall in $CO_2$ concentration. The tidal volume of each breath generally can vary, as shown in FIGS. 1A, 1B, 2B, and 3, although some of the breaths may be of the same or similar tidal volume. Preferably, the tidal volumes of the lungs may be separately accumulated or determined for each respiration event/CSR cycle (cluster of breaths such as peaks $V_1$, $V_2$, $V_3$, $V_4$), and the separate values may be summed for each CSR cycle to estimate total tidal volume $\Sigma V_i$ when calculating the fluid index for each CSR cycle. The plurality of fluid indices is then averaged.

Referring to FIGS. 1A, 1B, 2A and 2B, as the $CO_2$ concentration 107 in the blood increases toward maximum 108 of $CO_2$ following an apneic period 102, hyperventilation 104 begins, increasing the blood oxygen saturation level 106 as the patient begins to rapidly breathe. As hyperventilation 104 and inhalation continues, the tidal volumes of each breath $V_1$, $V_2$, $V_3$, $V_4$, $V_5$, $V_6$, $V_7$, $V_8$ can vary, such that each CSR cycle has a wax and wane pattern, or modulates. As the blood oxygen saturation level is reached, the $CO_2$ concentration decreases towards $CO_2$ minimum 110. When the breathing becomes shallower, such as before $V_4$ in FIG. 2B, another apneic period 102 begins, and the $CO_2$ concentration level begins to increase. As can be seen in FIGS. 1A, 1B, 2A, and 2B, there may be a small lag period between the beginning of apnea and when the CO2 concentrations begin to rise, and between hyperventilation and when oxygen saturation occurs. This lag period will vary from individual to individual. It may be necessary to obtain more data points to obtain the correct maximum-minimum value ($\Delta CO2$) corresponding to the matched CSR cycle.

As an alternative to intrathoracic impedance, another surrogate for lung volume is phrenic nerve sensing. The phrenic nerve is connected to the lung diaphragm. Thus, sensing of phrenic nerve activity as each breath is taken can also provide an estimate of lung tidal volume. A lead connected to an implantable medical device may have a sensor attached to the lead, such that the sensor is adjacent the phrenic nerve. The sensor may be used to sense activity or movement of the phrenic nerve. As the diaphragm expands upon inhalation, the phrenic nerve stimulates the lead, such that the sensor provides an estimate of the lung tidal volume.

Figure 4:
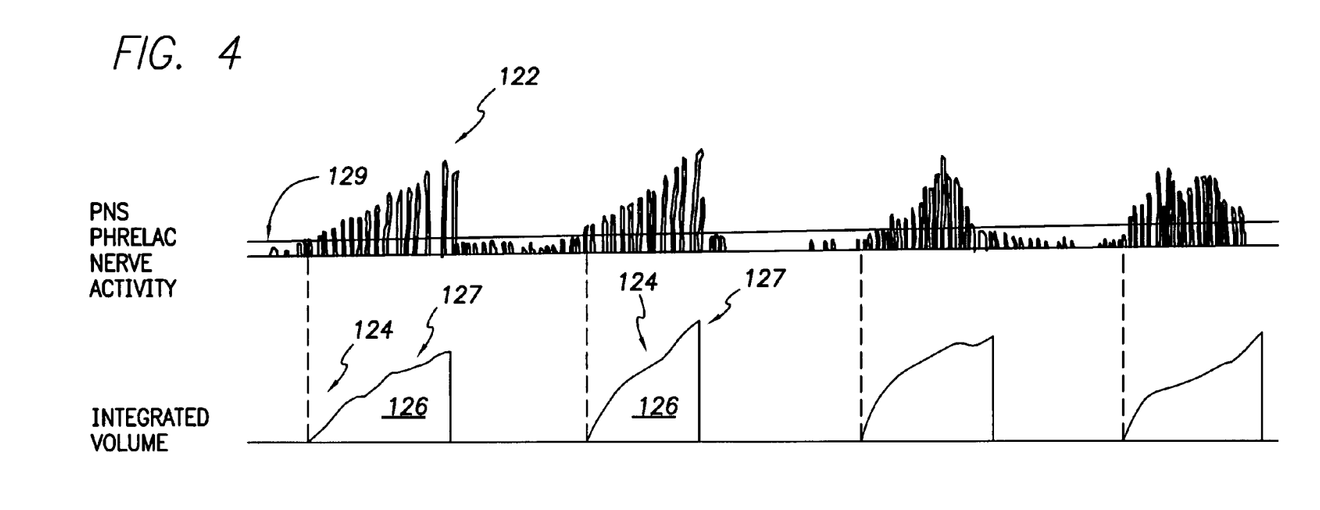
FIG. 4 is a graph illustrating phrenic nerve activity during Cheyne-Stokes respiration.

Referring to FIG. 4, as each breath is taken, as at 120, signals 122 are generated, indicating phrenic nerve activity. The signals are averaged over a selected period of time, such as for about one minute approximately every five (5) minutes during a 30 to 40 minute time period, usually once daily. Alternatively, a given number of inhalations may be used. The readings may be taken more or less frequently, as determined by the health care professional. Each respiratory effort produces a phrenic nerve value 124. The calculated area 126 under the substantially triangular shape 127 of phrenic nerve value 124 provides an estimate of the lung tidal volume, similar to $V_1$, $V_2$, $V_3$ and $V_4$ in FIG. 2B. Shape 127 may be shapes other than triangular, such as rectangular or semi-circular, with the area under the shape being calculated to determine the tidal volume. Shape 127 is generally determined based on the patient.

To determine whether to integrate the phrenic nerve activity, a desired noise threshold is selected so as to discriminate for the desired phrenic nerve activity. If the phrenic nerve activity is over that certain threshold 129, the signal is integrated. Preferably, the calculated area of 124 may be separately accumulated or determined for each respiration event/CSR cycle, or the separate maximum height values 128 may be used to estimate total tidal volume $\Sigma V_i$ when calculating the fluid index for each CSR cycle. The plurality of fluid indices is then averaged.

An external device, such as a pneumotachometer, can also be used to calibrate an implanted impedance sensor to estimate, measure or calibrate the lung tidal volume. The external pneumotachometer can send flow signals by wireless telemetry to the implanted device to correspond to the tidal volume. In addition, a thermistor cannula can measure the air flow exhaled over time to estimate or calibrate the tidal volume.

A lung fluid index reflecting the total lung volume required to remove a blood gas, such as $CO_2$, may be calculated using the following ratio:

$$\text{Fluid index} = \frac{\Delta CO_2}{\sum_{i=1}^{N} V_i}$$

where $\Delta CO_2$ is the difference between the maximum and minimum readings of the blood gas, such as $CO_2$, $\Sigma V_i$ is the summation of the lung tidal volumes determined, for instance, from intrathoracic impedance or phrenic nerve activity values, and i is from one breath to a number of breaths N during each CSR cycle. A lung fluid index for $O_2$ surrogates, such as saturated $O_2$, can also be calculated using the fluid index ratio above.

Figure 5A:
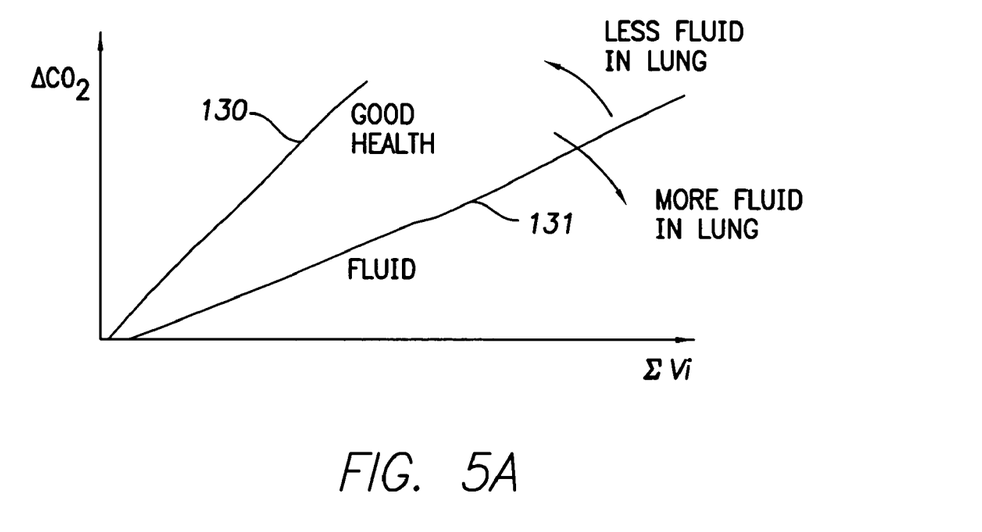
FIG. 5A is a graph of the lung fluid index for a patient in good health and in poor health.

One purpose of the respiratory organ (lungs) is to remove $CO_2$ from the body and to add $O_2$ to the body. When a patient is in good health, there is less fluid in the lungs. Thus, there is more area in the lungs for gas exchange. If the assumption is that $\Delta CO_2$ (swing from maximum to minimum) remains fixed, the healthy patient may only have to breathe a few breaths to remove the $CO_2$. Therefore, the summed total respiration or tidal volume ($\Sigma V_t$) to remove a given amount of $\Delta CO_2$ within a CSR cycle in a healthy patient will be less, as shown by the ratio or fluid index, or slope 130, in FIG. 5A. However, as the lungs become more congested in patients with CHF due to fluidic edema, it will take many more breaths to remove the $CO_2$ as compared to a healthier individual due to compromised gas exchange efficiency. Therefore, the summed total tidal volume ($\Sigma V_t$) must increase to remove the same amount of $\Delta CO_2$, as shown by the slope at 131. A decreased gas exchange area due to increased fluid in the lungs causes the need for increased total tidal volume. Therefore, the lung fluid index in a diseased patient tends to be less. The lung fluid index decreases as the patient's CHF condition deteriorates. The more congestion, the larger the tidal volume will need to be to remove the same amount of $\Delta CO_2$, which will be reflected in the ratio.

Figure 5B:
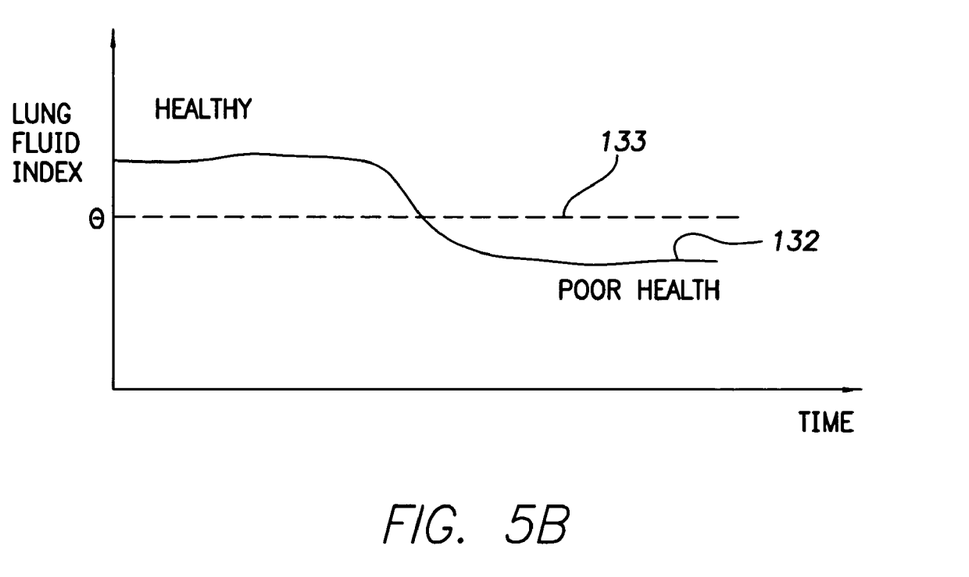
FIG. 5B is a graph of the lung fluid index over time for a patient in good health and in poor health.

This ratio is stored and used as a lung fluid index to assess the severity of fluid in the lungs. Referring to FIG. 5B, as long as the ratio remains over a certain threshold 132, the patient does not have to worry about the build up of fluid in the lungs. However, as the ratio decreases over time, the severity of the fluid in the lungs will need to be closely monitored. Long term threshold value 132 is determined over the long term and the short term threshold value 133 is determined over the short term. The short term average of threshold value 133 and long term average of threshold value 132 may be calculated each day. The difference D between the short term average and long term average threshold values may be determined by subtracting the short term average from the long term average ($D=Long_{av}-Short_{av}$) The long term average threshold value may be determined by averaging the threshold values for approximately the preceding thirty (30) days. The short term average threshold value may be determined by averaging the threshold values for approximately the preceding three (3) days. To prevent the long term average threshold value from becoming too low, a minimum limit may be imposed. A minimum limit is chosen as a fixed value so that it does not decrease as heart failure worsens. If the thirty (30) day long term average is lower than this minimum limit, this minimum limit is used as the long term threshold value. The trend in the patient's health condition can be monitored using these values. As D increases, the implanted medical device will be interrogated, and an alarm will be generated or go off, thereby alerting the physician and patient as to the worsening condition. Monitoring the fluid levels in the lungs, such as daily, will alert the patient and the physician as to any trends toward worsening pulmonary edema so that corrective action can be taken before the fluid level gets to a level requiring hospitalization of the patient.

The Cheyne-Stokes respiratory pattern can thus be detected by methods that measure metabolic gases and chemicals and recognize the oscillatory changes that occur over time scales consistent with the Cheyne-Stokes respiratory pattern, or methods that directly assess the mechanical changes in the thorax associated with breathing. This invention takes advantage of swing patterns of a blood gas, such as $CO_2$, during the Cheyne-Stokes respiratory pattern.

Many implantable medical devices provide data acquisition of physiological information from a human body. The implantable medical device can be housed within a hermetically sealed canister or housing, which may itself be conductive so as to serve as an electrode in the implantable medical device. One or more sensors/leads are electrically coupled to the implantable medical device and extended into the right atrium or right ventricle of the patient's heart. The implantable medical device may be, for example, cardiac systems including implantable heart monitors and therapy delivery devices, such as pacemakers, cardioverters, defibrillators (ICD), heart pumps, card iomyostimulators, ischemia treatment devices, and other heart therapy devices. The implantable medical device can also be a sleep apnea detection device, such as an intrathoracic impedance monitor or accelerometer mounted on or near the chest, or can be a dedicated fluid monitor. External devices have been discussed above (pneumotachometer and thermistor cannula).

Figure 6:
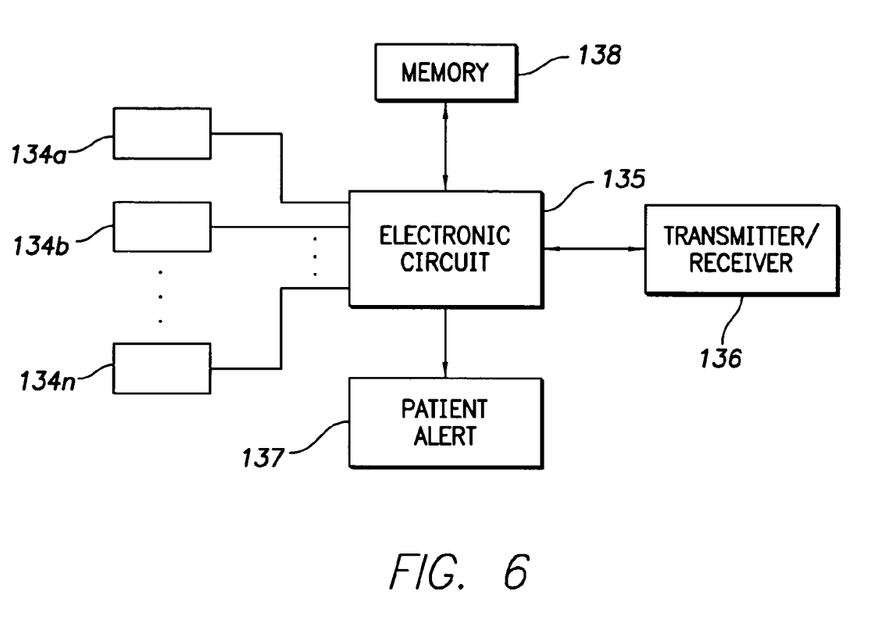
FIG. 6 is a functional block diagram of a preferred monitor of the invention.

A functional block diagram of an implantable medical device or monitor that can be used in the invention is shown in FIG. 6. One or a plurality of sensors 134a, 134b, . . . 134n is connected to an electronic circuit 135, which may be connected to a patient alert 137, transmitter/receiver 136, and memory 138, with each of elements 137, 136 and 138 being optional. In a preferred embodiment, the electronic circuit 135 includes a low-power microprocessor. In alternate embodiments, the microprocessor is excluded, or control and higher level processing is performed by a microcontroller, an embedded system, a programmable logic device such as a field-programmable logic array, or a combinatorial implementation of a state machine.

Figure 7:
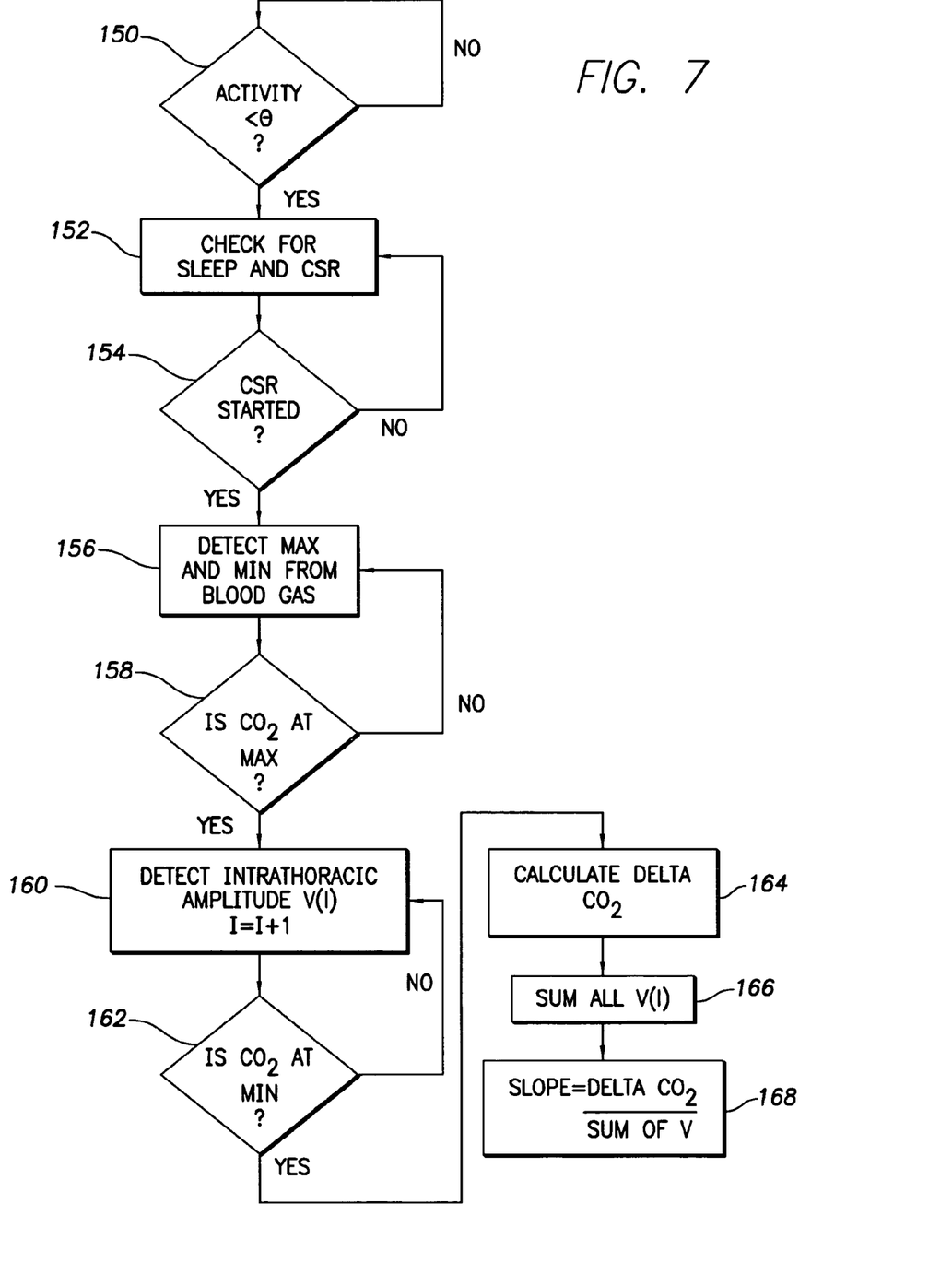
FIG. 7 is a flow chart of a method for determining lung fluid index.

In FIG. 7, a flow chart illustrating the process used to determine the lung fluid index reflecting total lung volume required to remove $CO_2$ from blood gas is shown. The electronic circuit need not necessarily acquire and process data continuously. Preferably, the electronic circuit contains a timer that periodically initiates data acquisition. In one aspect, one of the sensors is an accelerometer. The output of the accelerometer is used by the electronic circuit to condition data acquisition on the activity of the patient. In block 150, the activity level of the patient is determined. If the patient is awake, the algorithm waits. Data can be scheduled to be acquired and processed at a selected time interval, such as every night. If the patient is asleep, data is acquired at the scheduled time. If the activity of patient is not below a certain threshold, such as the patient is not asleep, the algorithm waits until the condition is met. If the activity of the patient is below the desired threshold, in block 152, a patient is checked to see if they have been asleep for a predetermined time interval and if there is CSR. The predetermined time period in block 152 can vary, such as for one half hour, or can be determined by the phase of sleep the patient is in. If the patient is not asleep or if CSR has not started, then data is acquired the next time the condition is satisfied. If the monitor detects that CSR has started at block 154, the maximum and minimum values of the selected blood gas are detected at block 156. For instance, if $CO_2$ is the selected blood gas, the monitor determines whether $CO_2$ is at a maximum at block 158. If the $CO_2$ is not at a maximum, then data is acquired the next time the condition is satisfied. If $CO_2$ is at a maximum, then the intrathoracic amplitude is detected at block 160. The surrogates of respiration or tidal volume, such as intrathoracic amplitude (impedance), is measured and summed until $CO_2$ is at a minimum at block 162. If the $CO_2$ is not at a minimum, the intrathoracic amplitudes continue to be measured until $CO_2$ is at a minimum value. Once the $CO_2$ minimum is determined, $\Delta CO_2$ (delta $CO_2$) is calculated at block 164 by subtracting the $CO_2$ at its minimum value from $CO_2$ at its maximum value. The tidal volumes are summed together at block 166. The lung fluid index or slope, which is the ratio of $\Delta CO_2$ over the sum of the tidal volumes, is determined at block 168. Alternatively, at block 160, phrenic nerve activity can be sensed rather than intrathoracic amplitudes, as discussed above. The tidal volumes estimated by the area under the shape of the phrenic nerve values or the separate maximum height values are summed at block 166.

The flow chart in FIG. 7 can be used to track the patient condition after each respiration event/CSR cycle, or can average the fluid index over multiple events to obtain a filtered number for purposes of monitoring patients.

Figure 8:
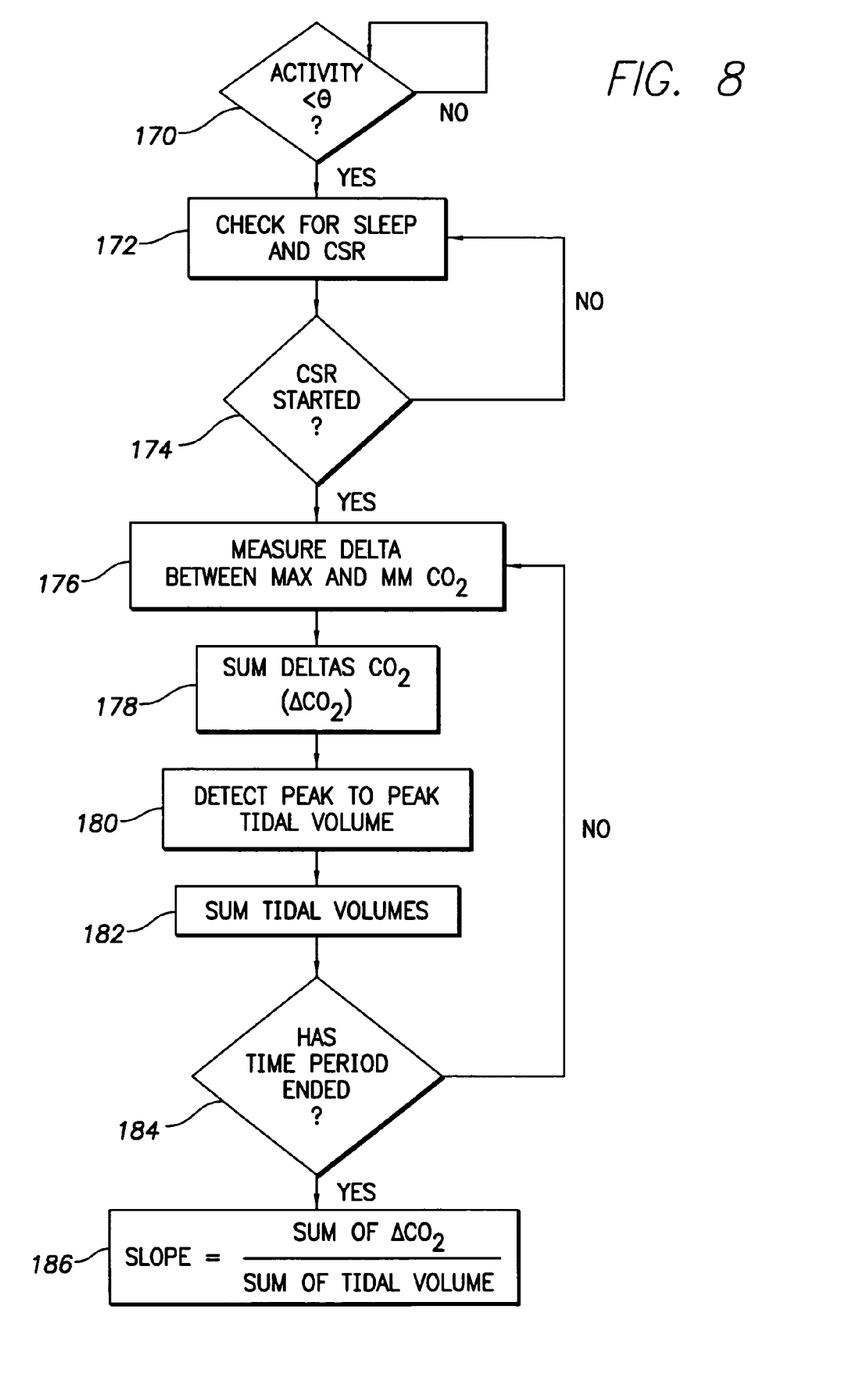
FIG. 8 is a flow chart of another method for determining lung fluid index.

In FIG. 8, a flow chart illustrating another process used to determine the lung fluid index reflecting total lung volume required to remove a blood gas for a selected period of time is shown. The electronic circuit need not necessarily acquire and process data continuously. Preferably, the electronic circuit contains a timer that periodically initiates data acquisition. In one aspect, one of the sensors is an accelerometer. The output of the accelerometer is used by the electronic circuit to condition data acquisition on the activity of the patient. In block 170, the activity level of the patient is determined. If the patient is awake, the algorithm waits. Data can be scheduled to be acquired and processed at a selected time interval, such as every night. If the activity of patient is not below a certain threshold, such as the patient is not asleep, the algorithm waits until the condition is met. If the activity of the patient is below the desired threshold, such as if the patient is asleep, data is acquired at the scheduled time. If the patient is not asleep, the algorithm waits until the condition is met. In block 172, a patient is checked to see if they have been asleep for a predetermined time interval and if there is CSR. The predetermined time period in block 172 can vary, such as for one half hour, or can be determined by the phase of sleep the patient is in. If the patient is not asleep or if CSR has not started, then data is acquired the next time the condition is satisfied. If the monitor detects that CSR has started at block 174, the maximum and minimum values of the selected blood gas are measured for a selected period of time, and the difference between the maximum and minimum values are determined at block 176. For instance, if $CO_2$ is the selected blood gas, the monitor determines the $CO_2$ maximum and $CO_2$ minimum over the time period, and $\Delta CO_2$ is calculated by summing all of the calculated differences of the $CO_2$ minimum values from the $CO_2$ maximum value over the time period. The $\Delta CO_2$ are summed at block 178. The tidal volumes are detected at block 180. Tidal volumes are summed together at block 182. At block 184, a determination is made whether the selected time period has ended. If it has not, then data is acquired the next time the condition is satisfied. If the selected time period has ended, the lung fluid index or slope, which is the ratio of the sum of $\Delta CO_2$ over the sum of the tidal volumes, is determined at block 186. Alternatively, at block 180, phrenic nerve activity can be sensed rather than intrathoracic amplitudes, as discussed above. The tidal volumes estimated by the area under the shape of the phrenic nerve values or the separate maximum height values are summed at block 182. The flow chart in FIG. 8 can average the fluid index over multiple events over a period of time to obtain a filtered number for purposes of monitoring patients.

The description of the invention including its applications and advantages as set forth herein is illustrative and is not intended to limit the scope of the invention, which is set forth in the claims. Variations and modifications of the embodiments disclosed herein are possible, and practical alternatives to and equivalents of the various elements of the embodiments would be understood to those of ordinary skill in the art upon study of this patent document. Other techniques may be used to determine the change in blood gas concentration ($\Delta CO_2$) or estimate the tidal volume. These and other variations and modifications of the embodiments disclosed herein may be made without departing from the scope and spirit of the invention.

Although the present invention has been described with reference to preferred embodiments, workers skilled in the art will recognize that changes may be made in form and detail without departing from the spirit and scope of the invention.

What is claimed is:

1. A method for use by an implantable medical device for assessing fluid level in a patient's lungs, comprising:
    detecting a first Cheyne-Stokes respiration cycle;
    obtaining a first transition value for a respiration-dependent blood parameter during the first Cheyne-Stokes respiration cycle, wherein the first transition value is representative of a change in blood gas levels within the patient during the first Cheyne-Stokes respiration cycle;
    obtaining a first tidal volume of the lungs value during the corresponding first Cheyne-Stokes respiration cycle;
    deriving a first fluid index for the first Cheyne-Stokes respiration cycle from the first transition value and the first tidal volume of the lungs value; and
    assessing fluid level in the lungs of the patient during Cheyne-Stokes respiration based on the first fluid index.

2. The method of claim 1 wherein:
    obtaining the first transition value comprises detecting a minimum value and a maximum value of $CO_2$ concentration and determining the change in blood gas levels within the patient from the minimum and maximum values of $CO_2$ concentration.

3. The method of claim 1 wherein:
    obtaining the first tidal volume of the lungs value comprises integrating phrenic nerve activity.

4. The method of claim 1 wherein:
    obtaining the first tidal volume of the lungs value comprises calibrating an impedance sensor from a pneumotachometer.

5. The method of claim 1 wherein:
    obtaining the first tidal volume of the lungs value comprises calibrating air flow from a thermistor cannula.

6. The method of claim 1 wherein:
    obtaining the first transition value comprises detecting a minimum value and a maximum value of $O_2$ concentration and determining the change in blood gas levels within the patient from the minimum and maximum values of $O_2$ concentration.

7. The method of claim 1 further comprising:
    detecting a second Cheyne-Stokes respiration cycle;
    obtaining a second transition value of a respiration-dependent blood parameter, the second transition value occurring during the second Cheyne-Stokes respiration cycle;
    obtaining a second tidal volume of the lungs value during the second Cheyne-Stokes respiration cycle;
    deriving a second fluid index for the second Cheyne-Stokes respiration cycle from the second transition value and the second tidal volume of the lungs value; and
    comparing the first fluid index and the second fluid index to obtain a further indication of the fluid level in the patient's lungs.

8. The method of claim 1 wherein obtaining the first tidal volume of the lungs value comprises summing intrathoracic impedance.

9. A method for assessing fluid level in a patient's lungs for use by an implantable medical device, comprising:
    detecting first and second periods of Cheyne-Stokes respiration;
    accumulating measurements of transitions in a respiration-dependent blood parameter during the first period of Cheyne-Stokes respiration, wherein the respiration-dependent blood parameter is representative of changes in blood gas levels within the patient during the first period of Cheyne-Stokes respiration;

accumulating measurements of tidal volume of the lungs during the first period of Cheyne-Stokes respiration;

deriving a first fluid index for the first period of Cheyne-Stokes respiration as a function of the accumulated measurements of transitions and from the accumulated measurements of tidal volume during the first period of Cheyne-Stokes respiration;

accumulating measurements of transitions in the respiration-dependent blood parameter during the second period of Cheyne-Stokes respiration;

accumulating measurements of tidal volume of the lungs during the second period of Cheyne-Stokes respiration;

deriving a second fluid index from the accumulated measurements of transitions in the respiration-dependent blood parameter and from the accumulated measurements of tidal volume during the second period of Cheyne-Stokes respiration; and assessing a fluid level in the lungs by comparing the first fluid index and the second fluid index.

10. A method of determining a fluid level in the lungs of a patient for use by an implantable medical device, comprising:

detecting a Cheyne-Stokes respiration (CSR) cycle;

determining a blood gas level in the patient during the CSR cycle;

determining a total tidal volume of the lungs of a patient during the CSR cycle;

deriving a fluid index for the CSR cycle based on the blood gas level and the total tidal volume of the lungs; and assessing a fluid level in the lungs of the patient based on the fluid index.

11. The method of claim 10 wherein the determining of the blood gas level comprises measuring a change in blood gas levels.

12. The method of claim 10 wherein the total tidal volume is determined using intrathoracic impedance.

13. The method of claim 10 wherein deriving a fluid index includes determining a ratio of a change in blood gas level to a tidal volume.

14. The method of claim 13 further including detecting an indication of the health of the patient by comparing the ratio against a predetermined threshold indicative of poor health.

15. The method of claim 14 further including alerting the patient if the ratio falls below the predetermined threshold indicative of poor health.

* * * * *